(12) United States Patent
Sevick-Muraca et al.

(10) Patent No.: US 9,167,240 B1
(45) Date of Patent: Oct. 20, 2015

(54) METHODS AND COMPOSITIONS FOR VALIDATION OF FLUORESCENCE IMAGING AND TOMOGRAPHY DEVICES

(71) Applicant: Board of Regents of the University of Texas System, Austin, TX (US)

(72) Inventors: Eva M. Sevick-Muraca, Houston, TX (US); Banghe Zhu, Houston, TX (US); I-Chih Tan, Houston, TX (US)

(73) Assignee: Board of Regents of The University of Texas System, Austin, TX (US)

( * ) Notice: Subject to any disclaimer, the term of this patent is extended or adjusted under 35 U.S.C. 154(b) by 0 days.

(21) Appl. No.: 14/104,846

(22) Filed: Dec. 12, 2013

Related U.S. Application Data

(60) Provisional application No. 61/736,343, filed on Dec. 12, 2012.

(51) Int. Cl.
| | |
|---|---|
| *G01D 18/00* | (2006.01) |
| *H04N 17/00* | (2006.01) |
| *B05D 5/06* | (2006.01) |
| *G01N 21/64* | (2006.01) |
| *G09B 23/28* | (2006.01) |

(52) U.S. Cl.
CPC .............. *H04N 17/002* (2013.01); *B05D 5/063* (2013.01); *G01N 21/6486* (2013.01); *G09B 23/286* (2013.01)

(58) Field of Classification Search
CPC .......... G01N 21/6486; H04N 13/0207; H04N 13/0239; H04N 13/0242; H04N 17/002; G09B 23/285; G09B 23/30; G09B 23/286; B05D 5/063

USPC ........................................................ 250/252.1
See application file for complete search history.

(56) References Cited

U.S. PATENT DOCUMENTS

| | | | |
|---|---|---|---|
| 7,198,901 B1* | 4/2007 | Rachlin ........................ 435/6.11 |
| 7,199,360 B1* | 4/2007 | Montagu ..................... 250/252.1 |
| 7,629,573 B2* | 12/2009 | Rice et al. ................... 250/252.1 |
| 2002/0098588 A1* | 7/2002 | Sammak et al. ..................... 436/8 |
| 2003/0087282 A1* | 5/2003 | Oshida et al. ....................... 435/6 |
| 2005/0074707 A1* | 4/2005 | Yamane et al. ................ 430/348 |
| 2006/0052565 A1* | 3/2006 | Yoshioka et al. ............... 528/10 |
| 2006/0184043 A1* | 8/2006 | Tromberg et al. ............. 600/476 |
| 2008/0038835 A1* | 2/2008 | Westphal et al. .............. 436/172 |
| 2008/0101657 A1* | 5/2008 | Durkin et al. ................. 382/110 |
| 2008/0103396 A1* | 5/2008 | Johnson et al. ............... 600/477 |
| 2008/0220982 A1* | 9/2008 | Vu ..................................... 506/9 |
| 2009/0065583 A1* | 3/2009 | McGrew ........................ 235/454 |
| 2009/0118622 A1* | 5/2009 | Durkin et al. ................. 600/473 |
| 2010/0168588 A1* | 7/2010 | Matsumoto et al. .......... 600/478 |
| 2010/0325761 A1* | 12/2010 | Nakata et al. .................... 850/33 |
| 2011/0177959 A1* | 7/2011 | Spain et al. ....................... 506/8 |

(Continued)

OTHER PUBLICATIONS

Author: John Baeten et al., Title:Development of fluorescent materials for Diffuse Fluorescence Tomography standards and phantoms, Date: 2007, Publisher:Optical Society of America.*

(Continued)

*Primary Examiner* — David J Makiya
*Assistant Examiner* — Taeho Jo
(74) *Attorney, Agent, or Firm* — Conley Rose, P.C.

(57) ABSTRACT

Methods and compositions are provided and include the construction of a simple solid phantom and a measurement approach for the quantification of excitation light leakage and measurement sensitivity of fluorescence imaging devices.

18 Claims, 13 Drawing Sheets

(56) References Cited

U.S. PATENT DOCUMENTS

| | | | |
|---|---|---|---|
| 2011/0211047 A1* | 9/2011 | Chhibber et al. | 348/47 |
| 2011/0286000 A1* | 11/2011 | Hu et al. | 356/445 |
| 2012/0034622 A1* | 2/2012 | Ignatius et al. | 435/7.2 |
| 2012/0204297 A1* | 8/2012 | Nakata et al. | 850/24 |
| 2012/0229891 A1* | 9/2012 | Liu et al. | 359/355 |
| 2013/0126757 A1* | 5/2013 | Sywe et al. | 250/459.1 |
| 2014/0147863 A1* | 5/2014 | O'Bryant et al. | 435/7.92 |

OTHER PUBLICATIONS

Author: Isabelle Noiseux et al., Title:Development of optical phantoms for use in fluorescence-based imaging, Date: 2010, Publisher:Design and Performance Validation of Phantoms Used in Conjunction with Optical Measurement of Tissue II, edited by Robert J. Nordstrom, Proc. of SPIE vol. 7567, 75670B.*

* cited by examiner

Qdots 800 fluorescence solid phantom

METHODS AND COMPOSITIONS FOR VALIDATION OF FLUORESCENCE IMAGING AND TOMOGRAPHY DEVICES

CROSS-REFERENCE TO RELATED APPLICATIONS

The present application claims the benefit of U.S. Provisional Application Ser. No. 61/736,343 filed Dec. 12, 2012, which is fully incorporated herein by reference.

STATEMENT REGARDING FEDERALLY SPONSORED RESEARCH OR DEVELOPMENT

This invention was made with U.S. Government support under Grant Nos. CA112679 and CA136404 awarded by the National Institutes of Health. The government has certain rights in the invention.

TECHNICAL FIELD

This disclosure relates to the use of a solid phantom in biomedical imaging. These phantoms that are needed to calibrate and evaluate the performance of fluorescence imaging camera systems methods and of algorithms used for processing the images produced. The provided methods and compositions can be used to determine sensitivity and performance of tomography and imaging devices, and thus validate operational readiness.

BACKGROUND

There are presently few technologies with the ability to non-invasively image the lymphatic system in vivo and in real time, and there is a paucity of imaging technologies with the sensitivity and temporal resolution to discriminate lymphatic function. Because lymph provides little endogenous contrast, lymphatic architecture and function cannot be probed directly with ultrasound, MR or CT techniques and the 2105-09701 lymphatic vasculature is not readily accessible for administration of the milliliters of contrast agent needed for MR or CT angiography, making aberrant lymph architecture difficult to routinely assess. Currently, lymphoscintigraphy which will visualize the structures involved but long integration times associated with gamma cameras prevent imaging of lymphatic function and the image resolution limits visualization of fine lymphatic vasculature. The ability to image lymphatic function non-invasively in animals and humans using near-infrared (NIR) fluorescence has been described for the purposes of detecting early signs of lymphedema following cancer treatment and evaluating the lymphatic response to lymphedema therapy (see for example, U.S. Pat. Nos. 5,865,754; 7,054,002; 7,328,059; US Patent Application Publication Nos: 2007/0286468; 2008/0056999; 2008/0064954; 2008/0175790 and 2011/007140). Non-invasive imaging of active lymph drainage, following intradermal administration of microgram amounts of indocyanine green (ICG), a green dye used for hepatic clearance and ophthalmological indications, has been done by using its NIR fluorescence properties for optical imaging. Another application for these imaging devices resides for intraoperative detection of disease markers that could demark tumor margins or cancerous tissues that would not otherwise be detected. The ability to use a phantom to determine whether the device and the molecularly targeted fluorescent imaging agent can together provide adequate signals for optimal performance requires validation with a stable phantom.

In yet another application, far red gene reporters are being used to demark diseased tissues in preclinical animal models in drug discovery programs. A phantom to underscore the performance and robustness of the imaging results so as to draw robust research conclusions is needed. That is to say a phantom that can provide a reflectance standard.

Consequently, there is continuing interest in fluorescence based non-invasive imaging methods such as NIR, far-red fluorescence and imaging agents for dynamically assessing lymph function in vivo to facilitate, direct and evaluate therapies for the treatment of lymphatic disorders and image guided therapies. However there has been little work to assess the performance of either time-dependent or time-independent measurement systems designed to collect fluorescence emanating from intact biological tissues. In addition, there are no metrics for assessing the sensitivity of such fluorescence imaging systems currently deployed in clinical studies. Because of the rapid evolution of fluorescence devices such as NIR, for use in humans, there are no metrics for assessing the sensitivity of these fluorescence imaging systems and a clear and unmet need to characterize devices, evaluate measurement sensitivity, especially when translating into humans with different imaging devices.

BRIEF SUMMARY

Methods and compositions are provided that allow the establishment of objective metrics for assessing the sensitivity of fluorescence detection and imaging camera systems. These compositions and methods facilitate the quantitative characterization of fluorescence detection and imaging camera systems that collect fluorescence from the surface which is illuminated with excitation light. The compositions and methods therefore provide the ability to evaluate, among other parameters, the sensitivity of instrumentation. In some embodiments, a method is provided comprising preparing a solid phantom, placing the solid phantom under a fluorescence imaging camera system, measuring reflected and scattered excitation light and fluorescent light from different portions of the phantom, determining the proportion of fluorescent versus reflected and scattered excitation light collected and computing a ratio of fluorescent versus reflected and scattered excitation light to ascertain level of sensitivity of the system. Such measurements provide objective standards that can be used to, among other things, determine whether the performance of the detection system is satisfactory for use on systems with which multiple scattering occurs, such as living tissues, for determining the performance of fluorescence detection imaging systems, for installation and operational qualification of fluorescence detection and imaging, comparison between systems, and day to day validation that the system is operating up to standard (quality control). While the technology is exemplified using qualification of NIR fluorescence imaging of the human lymphatics, it may also be used for qualification of NIR fluorescence imaging of other tissues as well as for qualification of fluorescence imaging systems that employ fluorescent proteins and molecules outside of the NIR wavelength range. These and other embodiments, features and advantages will be apparent in the detailed description and drawings which follow.

DETAILED DESCRIPTION

Figure 1:
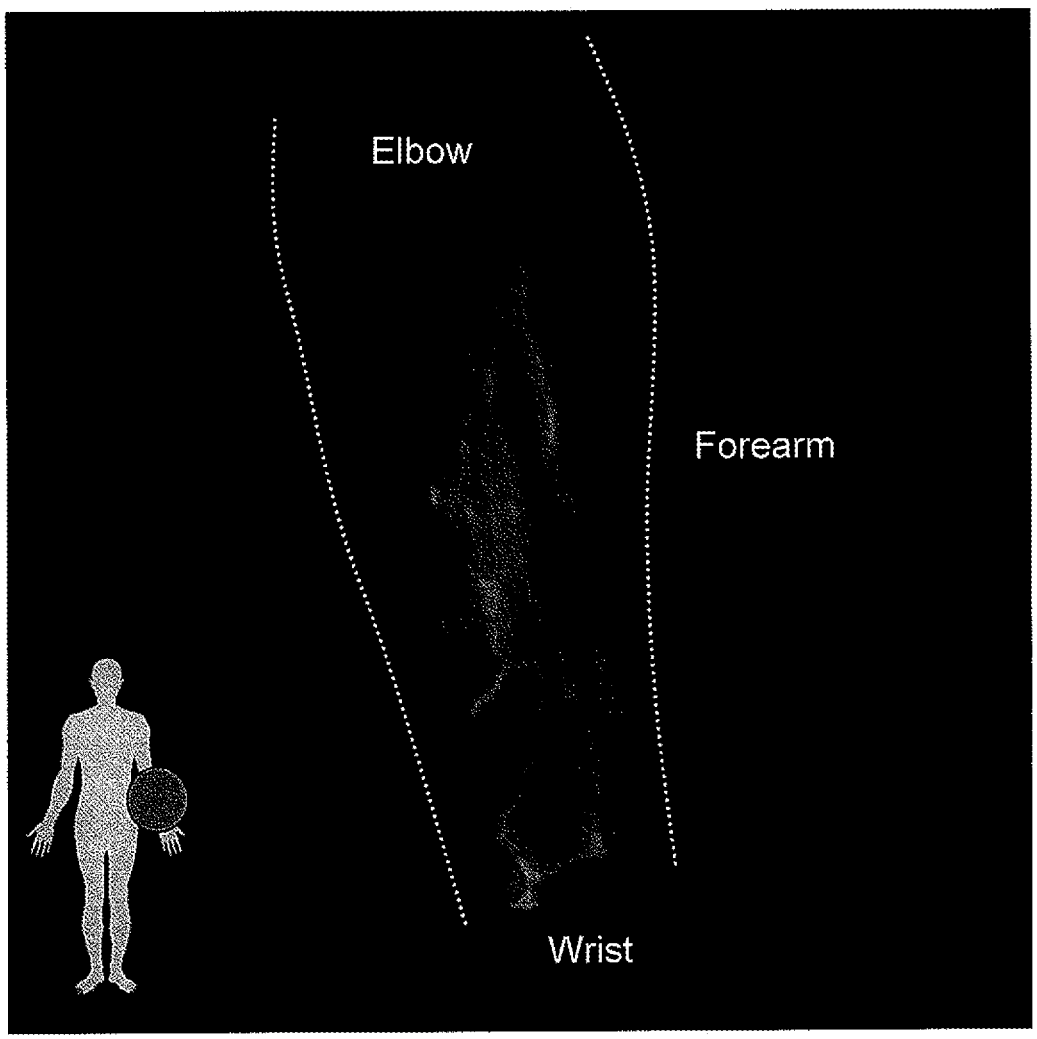
FIG. 1: Illustrates NIR fluorescence images of lymphatics of left arm of control subject. Black spots are covered injection sites to prevent oversaturation of the detection system.

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

DEFINITIONS

In this disclosure, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass either elements, or components comprising one unit and elements or components that comprise more than one unit unless specifically stated otherwise. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.14, and so forth). The term "about," when used in conjunction with a percentage or other numerical amount, means plus or minus 10% of that percentage or other numerical amount. For example, the term "about 80%," would encompass 80% plus or minus 8%.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials defines a term in a manner that contradicts the definition of that term in this application, this application controls.

As used herein, the term "near-infrared" refers to electromagnetic radiation at wavelengths ranging from about 750 nm to about 900 nm.

As used herein, and unless otherwise specified, the term "functional imaging" of lymph structures refers to how the structures function in terms of update of dye, the lymphatic flow as determined by the dye, dynamics of flow, and direction of flow of lymph and the associated materials carried by it. The function of the lymphatic structures can be described by lymph velocity, period or frequency of propulsive events, permeability, and other parameters that provide evidence of dysfunction in comparison to normal function imaged in healthy control animals or human subjects.

As used herein, and unless otherwise specified, a "phantom" or "imaging phantom" is a specially designed object that refers to a stable, reproducible, and pertinent model of the test article, which in this case is biological tissue, that can be imaged to evaluate, analyze, and tune the performance of a imaging and detection device.

As defined herein a fluorescence imaging or collection device refers to a system which illuminates the surface of multiply scattering systems, such as biological tissues, with excitation light, and which collects the generated fluorescence from the surface, sub-surface, or deeper portions of the tissue. As defined herein, scattering is the general physical process where some forms of radiation, such as light, are forced to deviate from a straight trajectory by one or more localized non-uniformities in the medium through which they pass.

Description

Fluorescence based imaging devices with high measurement sensitivity require fluorescence imaging agents that can be employed at minimal dosages to provide a greater margin of safety. Under current imaging techniques, the gain of fluorescence devices is often increased until a signal is registered; however in the absence of clearly defined fluorescent structures; it is often difficult to determine whether the observed signal is real or an artifact resulting from the excitation light leakage. Further, there are no metrics for assessing the sensitivity of NIR fluorescence imaging systems currently deployed in clinical studies.

With the aid of indocyanine green (ICG), lymphatic architecture and function in both mice and humans has been successfully imaged non-invasively using near-infrared (NIR) fluorescence imaging devices. Maximal measurement sensitivity of NIR fluorescence imaging devices is needed for "first-in-humans" molecularly targeting NIR fluorescence agents that are brighter than non-specific ICG. Herein a solid phantom and measurement approach for the quantification of excitation light leakage and measurement sensitivity of NIR fluorescence imaging devices is disclosed. The constructed solid phantom, consists in some embodiments of quantum dots impregnated onto specularly reflective surface, shows long-term stability and can be used as a traceable fluorescence standard. With the constructed solid phantom, the intensified CCD (ICCD)-based device demonstrated more than 300% higher measurement sensitivity compared to the Electron Multiplying CCD (EMCCD) based device when integration time was maintained less than 1.0 s.

Fluorescent materials emit light following the absorption of light (electromagnetic radiation). A Fluorescent semiconductor material is a solid matter which acts as a semiconductor with electronic properties and releases light following illumination with a different color light. A stable traceable phantom comprising of a reflectance standard, and such a stable fluorescent material is described herein.

Fluorescent materials comprise fluorescent metals, fluorescent semiconductor material, organic and inorganic fluorescent quantum dots (such as, but not limited to, Qdot® 800 ITK™), as well as organic and inorganic materials such as, but not limited to, Alexa Fluor, IR-Iodide, or lanthanide. Methods of using such a phantom to routinely evaluate imaging device performance are also presented herein. Such a phantom provides a stable, reproducible, and pertinent model of the test article (in this case, the test article is multiple scattering biological tissues that is being interrogated by the fluorescence imaging or detection device). The phantom must be stable to provide a quantifiable measurement (such as the reflectance value) that can be used to predict the performance of the fluorescence imaging or detection equipment under real conditions (i.e., accuracy of measurement of fluorescence from biological tissues). Because the model has constant scattering properties that may represent an upper bound of what can be expected in biological tissues, and because the phantom contains a stable fluorescent entity, is can create a signal that like biological tissues consists of reflected excitation light and fluorescence.

The phantoms described herein are manufactured in a reproducible and controlled manner such that they are more readily available and provide more consistent results than the use of a living subject, biological tissues, or cadaver, and likewise avoid subjecting a living subject to direct risk. These phantoms are stable and provide a quantifiable measurement that can be used to predict the performance of the fluorescence imaging or detection equipment under real conditions (i.e., accuracy of measurement of fluorescence from biological tissues). Because the model has constant scattering properties that may represent an upper bound of what can be expected in biological tissues, and because the phantom contains a stable fluorescent entity, it can create a signal that like biological tissues consists of reflected excitation light and fluorescence. These phantoms can be manufactured in a reproducible and controlled manner such that they are more readily available and provide more consistent results than the use of a living subject, biological tissues, or cadaver, and likewise avoid subjecting a living subject to direct risk.

The phantoms were specially designed such that when the surface is imaged it can be used to evaluate, analyze, and tune the performance of a fluorescent imaging and detection devices. These phantoms are easily generated but they lack the range or depth that many imaging phantoms often have and were not designed to give an illusion or depth per se. They are therefore referred to as being 2-dimensional (2-D), where for example the phantom in one embodiment is a piece of flat glass coated with q-dots, unlike a typical three dimensional imaging phantom such as a gelatin arm or head, as known in the prior art.

As described in the examples below these phantoms were used to demonstrate the superior imaging sensitivity of Intensified CCD (ICCD) cameras over Electron Multiplying CCD (EMCCD) cameras for NIR fluorescence imaging as reflected by signal-to-noise ratio (SNR). Since Electron Multiplying CCD (EMCCD) cameras cannot be modulated to efficiently conduct time-dependent measurements, and since the plethora of imaging devices currently use continuous wave (CW) measurements the presently described comparison of Intensified CCD (ICCD) and Electron Multiplying CCD (EMCCD) to planar, continuous wave (CW) measurements. The comparison can be extended to time-dependent methods using a pulse of excitation light, intensity modulated excitation light, or any time-varying excitation light.

The ability to quantify and minimize excitation light leakage using a traceable phantom or standards will increase the reliability and value of clinical fluorescence imaging. Presently exemplified is a solid phantom created using quantum dot-based fluorescence and its use to characterize excitation light leakage and measurement sensitivity in fluorescence imaging devices. For example, the fluorescent solid phantom described can be created using organic quantum dots (Qdot® 800 ITK™, as detailed in the examples) or it can be constructed using other stable fluorescent material, including, but not limited to, fluorescent metals, fluorescent semiconductor material, organic and inorganic quantum dots as well as organic and inorganic materials such as, but not limited to, Alexa Fluor, IR-Iodide, or lanthanide as a replacement depending on the operating wavelengths of the fluorescence imaging device in which it is to be used. It would be apparent to those of skill in the art to use appropriate solvents and resins (such as but not limited to polyurethane, polyester resin and epoxy-resins) to adapt the present methods and composition to the fluorescence imaging device.

Quantum dots are a product of Ocean NanoTech (Springdale, Ark., USA) and are available as core and core-shell quantum dot powder, colloidal dispersion in organic solvent, and colloidal dispersion for dispersion in aqueous solution. Quantum dots (QDs) are fluorescent semiconductor nanocrystals that have high photoluminescent quantum yields with size tunable emission wavelength, are resistant to photobleaching, and allow simultaneous excitation of multiple colors from a single light source. The solid phantom constructed was stable and then used to qualify the higher measurement sensitivity of the Intensified CCD (ICCD)-based fluorescence imaging devices, as opposed to Electron Multiplying CCD (EMCCD)-based fluorescence imaging devices. The phantom was used to assess the calculated transmission ratio (R) and signal to noise ratio (SNR). In general, the constructed fluorescence solid phantom should be stored in a dry, dark location to avoid the possibility that the fluorescence phantom will decay when exposed to a light environment for a long time (for example, one month). However, it is noteworthy that for qualification of a specific fluorescence imaging device, the constructed phantom only needs to be exposed under light conditions for a few minutes. Therefore, the constructed quantum dot based solid phantom and the methodology for measuring parameters of transmission ratio and signal to noise ratio (SNR) can be used as a standard and quantifiable metric for installation and operational qualification of CCD, Electron Multiplying CCD (EMCCD) and Intensified CCD (ICCD) based fluorescence imaging devices. For example, the fluorescent solid phantom created using organic quantum dots could have been constructed using other stable fluorescent material, including, but not limited to, fluorescent metals, fluorescent semiconductor material, organic and inorganic fluorescent quantum dots, as well as organic and inorganic materials such as, but not limited to, Alexa Fluor, IR-Iodide, or lanthanide as a replacement depending on the operating wavelengths of the fluorescence imaging device in which it is to be used.

For those using a time-dependent measurement approach such as frequency domain photon migration (FDPM), the transmission ratio (R) and signal-to-noise ratio (SNR) can be calculated with the measured DC intensity and AC amplitude. For those with the point illumination and area collection geometry the chosen region of interest (ROI) may or may not include the illumination point.

Methods and compositions are therefore provided that establish objective metrics for assessing sensitivity of fluorescence imaging and detection systems used to interrogate systems that contain sources of multiple scatter, such as, but not limited to biological tissue. These methods and compositions allow the characterization of the devices and evaluating the measurement sensitivity. This greatly facilitates device to device comparison as well as aids in the establishment of quality control standard for fluorescence imaging devices, such as but not limited to NIR fluorescence imaging devices, intended for use in living tissues and biological specimens obtained from, for example, animals or humans.

Figure 2:
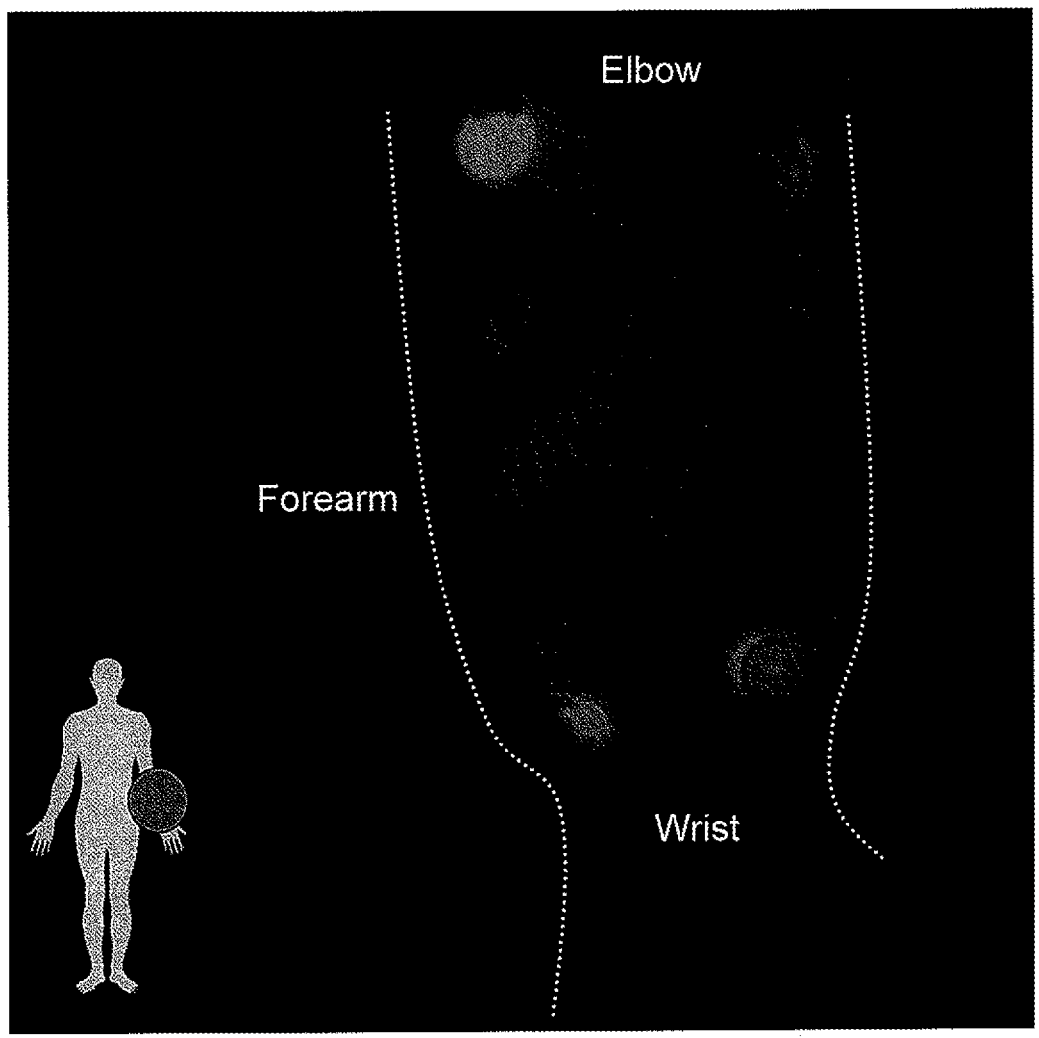
FIG. 2: Illustrates NIR fluorescence images of diseased lymphatics in left arm lymphedema subject. Black spots are covered injection sites to prevent oversaturation of the detection system.

The utility of such phantoms in a clinical application of NIR fluorescence imaging of human lymphatics which begins with 0.1 cc intradermal injections containing 25 ug of a dim NIR fluorophore, indocyanine green (ICG) is demonstrated in the examples below. The ICG-laden lymph fluid rapidly enters the lymphatic capillary plexus and transits through lymphatic vasculature and lymph nodes. By illuminating tissue surfaces with dim 785 nm laser diode light and collecting the emanating, 830 nm fluorescent signal with an intensified charged coupled device (ICCD), consecutive images of lymphatic contractile flow are acquired. FIG. 1 shows a typical, recent example of the lymphatic vasculature and function in the arms of a normal volunteer. FIG. 2 shows an example of aberrant lymphatic architecture and function in a subject diagnosed with lymphedema. This technology has been rapidly developing continual improvements in the sensitivity of the instrumentation in anticipation of molecularly targeting NIR fluorescence agents and three-dimensional NIR fluorescence tomography for use in humans.

Typically, continuous wave (CW) NIR fluorescence measurements are conducted with an Electron Multiplying CCD (EMCCD) rather than an intensified CCD (ICCD), both of which have different noise characteristics owing to their different in gain mechanisms. In addition, the resolution of images acquired by intensified CCDs (ICCDs) is limited by the spatial resolution of the intensifier multichannel plate and can be dramatically inferior to Electron Multiplying CCDs (EMCCD). There has been little work to assess the performance of either time-dependent or time-independent measurement systems designed to collect NIR fluorescence emanating from biological tissues. In addition, there are no metrics for assessing the sensitivity of fluorescence imaging systems currently deployed or in the future to be employed in clinical studies. In some embodiments of fluorescence imaging systems, when a measurement is taken there is no however, the noise floor associated with leakage of reflected light "looks like" fluorescence when it really is not, hence, a diagnostic decision could be rendered inappropriately. The only way to validate the device is thus to perform an operational qualification prior to each use on a well-defined standard that does not change with time. The present disclosure provides a "noise floor" that limits the sensitivity of fluorescence imaging from tissues and the differences in gain mechanisms that define noise levels in Electron Multiplying CCD (EMCCD)-based devices and intensified CCD (ICCD)-based devices. Also described is a solid phantom for characterization of excitation light leakage and measurement sensitivity that can be used to compare imaging devices and to provide a robust standard for validation in manufacturing and for operational qualification prior to clinical use. The solid phantom has been used to compare the figures of merits of (i) the transmission ratio (R) and (ii) signal to noise ratios (SNRs) of Electron Multiplying CCD (EMCCD) and intensified CCD (ICCD)-based devices in order to compare their performance on biological tissues. Also described is the importance of device sensitivity for molecularly targeted NIR fluorescence agents and a methodology for operational quality assessment using the presently disclosed solid phantom system.

NIR fluorescence imaging and tomography are accomplished using integrating camera systems based upon a charge-coupled device (CCD), Electron Multiplying CCD (EMCCD), or Intensified CCD (ICCD). The measurement sensitivity of fluorescence imaging systems is in mainly governed by (i) the quantum efficiency of CCD chip and intensifier, (ii) gain for Electron Multiplying CCD (EMCCD) and Intensified CCD (ICCD) cameras, (iii) various noise sources in the CCD cameras, and (iv) the leakage of ambient and excitation light through the optical filters that may be used to selectively pass the generated fluorescence light. Alternatively wavelength sensitive intensifiers and CCDs can also be used to selectively collect fluorescence, but neither of the filters for detection devices are perfect at wavelength discrimination between excitation and fluorescence. In current instrumentation, excitation light leakage may arise from one or more of the following: (i) broad band illumination sources or laser diode sources that have side-band components located at the emission wavelength that is selectively passed by the optical filters; (ii) limited optical densities of the filters at undesired wavelengths; and (iii) the spectral "blue shifted" performance of filters that arises due to the multiply scattered, non-normal, incident light (as illustrated in Hwang, K., Houston, J. P., Rasmussen, J. C., Joshi, A., Ke, S., Li, C. & Sevick-Muraca, E. M. Improved excitation light rejection enhances small-animal fluorescent optical imaging. *Mol Imaging* 4, 194-204, 2005 and Zhu, B., Rasmussen, J. C., Lu, Y. & Sevick-Muraca, E. M. Reduction of excitation light leakage to improve near-infrared fluorescence imaging for tissue surface and deep tissue imaging. *Med Phys* 37, 5961-5970, 2010). With the optimized filter permutation and appropriate illumination sources, excitation light leakage can be reduced to improve measurement sensitivity (as demonstrated in Zhu, B. & Sevick-Muraca, E. M. Minimizing excitation light leakage and maximizing sensitivity for molecular imaging with near-infrared fluorescence. *J Innov Opt Health Sci* 4, 301-307, 2011). Yet there is no satisfactory means to quantify the improvement and to compare the performance of imaging instrumentation.

Transmission ratio for quantifying excitation light leakage: To quantify excitation light leakage of imaging devices, a previously described method to measure excitation light leakage was used (described for example in Hwang, et al., 2005, ibid; Zhu, et al., 2010, ibid; Zhu, et al., 2011, ibid) Excitation light leakage is defined as the signal $S(\lambda_x)$, or the collected, average pixel intensity values over a fixed region of interest (ROI) associated the image of the scattering surface that arises exclusively of excitation light which has "leaked" through filters. It is effectively the "false" signal that can be measured from the images of a phantom without a fluorescent source following illumination at the excitation wavelength. When the fluorescent dye is present, the collected average pixel intensities over a ROI of the same value of area as $S(\lambda_x)$ was measured and represents both the fluorescent signal as well as the "leaked" excitation light and are defined as $S(\lambda_{x+}\lambda_m)$. Measurement settings such as integration time, gain and laser power were held constant for collection of signals $S(\lambda_x)$ and $S(\lambda_{x+}\lambda_m)$ from phantoms without and with fluorescent dye present. Other system effects that may add to noise level are typically removed through an additional subtraction of the mean ambient noise (obtained without illumination of excitation light). The transmission ratio R is then calculated using the following equation:

$$R = \frac{S(\lambda_x)}{S(\lambda_x + \lambda_m) - S(\lambda_x)} \quad [1]$$

Where $S(\lambda_x)$ signals are the "off-band" collected signals, whereas $S(\lambda_x+\lambda_m)-S(\lambda_x)$ represent the "in-band" collected signals. A lower value of the transmission R signifies less excitation light leakage.

Signal-to-Noise Ratio of NIR Fluorescence Imaging System:

The performance of a system is represented by the amalgamation of components, including illumination source, camera, and optical filters. In order to quantify the measurement sensitivity of NIR fluorescence imaging systems, the signal to noise ratio (SNR) can be calculated using the following equation:

$$SNR = 20 \text{Log} 10 \left( \frac{F_{counts}}{N_{counts}} \right) \quad [2]$$

where $F_{counts}$ is the average pixel count of the signals from a fluorescence phantom over a region of interest (ROI), and $N_{counts}$ represents the average pixel count of background signals taken from a non-fluorescent region of interest (ROI). Measurement settings such as integration time, gain, and laser power are held constant for collection of $F_{counts}$ and $N_{counts}$.

While NIR systems have been previously characterized with the parameters using a liquid intralipid/ICG phantom, a traceable, solid phantom is needed, especially for operational qualification measurements that are conducted in the clinic. The present stable and potentially National Institute of Standards and Technology (NIST) traceable phantom comprises a reflectance standard and stably fluorescent semiconductor material such as but not limited to quantum dots (such as Qdot® 800 ITK™) to routinely evaluate imaging device performance. This solid phantom was also used to show the superior imaging sensitivity of Intensified CCD (ICCD) cameras over Electron Multiplying CCD (EMCCD) cameras for NIR fluorescence imaging as reflected by SNR.

Because of the rapid evolution of NIR fluorescence devices for use in humans, there is a clear need to characterize devices and develop a figure of merit for evaluating measurement sensitivity, especially when translating into humans with different imaging devices.

In some embodiments the described methods and compositions, allow the objective determination of operational readiness of a machine for use following installation of the system as well as for day to day quality control. In some embodiments, they also facilitate objective comparison between different fluorescence imaging camera systems, as well as machine to machine variation within a particular fluorescence imaging camera system. In some embodiments, the methods and compositions make possible, the identification of operator to operator variability and can also be used to facilitate training and qualification of individual operators. Such measurements also allow comparison of fluorescent dye efficacies in a particular fluorescence imaging camera systems, those allowing optimization of the entire process of fluorescence medical imaging. The ability to carry out such analysis is critical, for example to the use of NIR fluorescence medical imaging for the imaging of lymphatic system structure and functional activity and in human patients. It will also be critical to the use of fluorescence medical imaging, whether for intraoperative guidance, pathological examination of resected tissues, or small animal imaging, that employ exogenous fluorescent imaging agents.

In some embodiments, provided is a solid phantom for use with fluorescence imaging camera systems. In some embodiments, the phantom comprises a suspension of stable fluorescent material, including, but not limited to, fluorescent metals, fluorescent semiconductor material, organic and inorganic fluorescent quantum dots, as well as organic and inorganic materials such as, but not limited to, Alexa Fluor, IR-Iodide, or lanthanide layered at varying densities onto a calibrated diffuse reflectance target. In some embodiments, the phantom further comprises polyurethane or other coating which can be used to retain stable fluorescent material, including, but not limited to, fluorescent metals, fluorescent semiconductor material, organic and inorganic fluorescent quantum dots, as well as organic and inorganic materials such as, but not limited to, Alexa Fluor, IR-Iodide, or lanthanide and reflectance material and thus retain both scattering and fluorescent entities on the surface of the phantom. In some embodiments, the stable fluorescent material, including, but not limited to, fluorescent metals, fluorescent semiconductor material, organic and inorganic fluorescent quantum dots, as well as organic and inorganic materials such as, but not limited to, Alexa Fluor, IR-Iodide, or lanthanide is painted on a calibrated diffuse reflectance target. In some embodiments, the stable fluorescent material, including, but not limited to, fluorescent metals, fluorescent semiconductor material, organic and inorganic fluorescent quantum dots, as well as organic and inorganic materials such as, but not limited to, Alexa Fluor, IR-Iodide, or lanthanide is sprayed on the calibrated diffuse reflectance target. In some embodiments, the calibrated diffuse reflectance target is dipped in a solution comprising the stable fluorescent material, including, but not limited to, fluorescent metals, fluorescent semiconductor material, organic and inorganic fluorescent quantum dots, as well as organic and inorganic materials such as, but not limited to, Alexa Fluor, IR-Iodide, or lanthanide. In some embodiments, the reflectance value of the target is 99%, 98%, 97%, 96%, 95%, 90%, 85%, 80%, 75%, 70% 65%, 60%, 55%, 50%, 25%, 10%, 9%, 8% 7%, 6%, 5%, 4%, 2%, 1% or 0% (% of for example, incident light that is reflected) and mimics the worse-case scenario of multiply scattered light that contributes to excitation light leakage and poor instrument performance. In some embodiments the method of making a solid phantom comprises: (i) preparing a 1.0 uM solution of the stable fluorescent material, including, but not limited to, fluorescent metals, fluorescent semiconductor material, organic and inorganic fluorescent quantum dots, as well as organic and inorganic materials such as, but not limited to, Alexa Fluor, IR-Iodide, or lanthanide; (ii) diluting with a polyurethane solution to a first concentration, wherein the first concentration may be in some embodiments 0.001 uM to about 10 um, 0.001 uM to about 1 uM, or preferably about 0.1 uM; (iii) coating the reflectance target such that the reflectance value of the target simulates just less than 100% reflectivity, which represents the worse-case scenario for multiply scattered light that contributes to excitation light leakage. A reflectance standard provides reflected incident light. For example a reflectance standard of 99.99% literally reflects or scatters back 99.99% of the incident light that could be collected by the fluorescence imaging. A reflectance standard has a reference value of 90.00%, i.e will reflect 90.00% of the incident light that could be collected by the fluorescence imaging and detection system, and thus constitutes an "excitation light leakage." Biological tissues can reflect between 10-99.99% of incident light, depending upon the wavelength employed. Therefore, by using a reflectance standard of 99.99% (i.e having a reflectance value of 99.99%), the phantom represents the worse-case scenario for excitation light leakage using a fluorescence imaging system.

In some embodiments, the stable fluorescent material, including, but not limited to, fluorescent metals, fluorescent semiconductor material, organic and inorganic fluorescent quantum dots, as well as organic and inorganic materials such as, but not limited to, Alexa Fluor, IR-Iodide, or lanthanide are sprayed on a calibrated diffuse reflectance target. In some embodiments, the calibrated diffuse reflectance target is dipped in a solution comprising the stable fluorescent material, including, but not limited to, fluorescent metals, fluorescent semiconductor material, organic and inorganic fluorescent quantum dots, as well as organic and inorganic materials such as, but not limited to, Alexa Fluor, IR-Iodide, or lanthanide. In some embodiments, the reflectance value of the surface density of stable fluorescent material, including, but not limited to, fluorescent metals, fluorescent semiconductor material, organic and inorganic fluorescent quantum dots, as well as organic and inorganic materials such as, but not limited to, Alexa Fluor, IR-Iodide, or lanthanide located on the surface of the reflectance standard (or reflectance value) is between 99 and 0% (inclusive, for example, 99%, 98%, 97%, 96%, 95%, 90%, 85%, 80%, 75%, 70% 65%, 60%, 55%, 50%, 25%, 10% or 0%) designed to mimic the range of fluorescent signals that can be expected from biological tissues. The worse-case scenario for multiply scattered light that contributes to excitation light leakage is a phantom with 99.99% reflectance (value) and 0% surface density in which all the measured light would constitute excitation light leakage and the noise floor.

In some embodiments, a method of quantitatively characterizing the transmission ratio and the signal-to-noise ratio of fluorescence imaging camera system, the method comprising: (i) placing the solid phantom under the fluorescence imaging camera system; (ii) determining the transmission ratio to quantify excitation light leakage; (iii) determining the signal-to-noise ratio. In some embodiments, a method of evaluating the sensitivity of a fluorescence imaging camera system, the method comprising: (i) placing the solid phantom under the fluorescence imaging camera system; (ii) imaging or measuring the reflected excitation light from a surface of the phantom without quantum dots to determine a parameter of $S(\lambda_x)$; (iii) imaging or measuring fluorescence from different surface portions of the phantom that have >0% density coverage of stable fluorescent material, including, but not limited to, fluorescent metals, fluorescent semiconductor material, organic and inorganic fluorescent quantum dots, as well as organic and inorganic materials such as, but not limited to, Alexa Fluor, IR-Iodide, or lanthanide to determine a parameter of to determine a parameter of $S(\lambda_x+\lambda_m)$; and (iv) computing a transmission ratio R and SNR (see equation 1 and 2) to ascertain the level of sensitivity of the system. In some embodiments, provided are methods of validating that a fluorescence imaging camera system is operating at an acceptable level.

In some embodiments, provided are methods of validating that a fluorescence imaging camera system is operating at an acceptable level. In some embodiments, a method of comparing two or more fluorescence imaging camera systems, the method comprising: (i) obtaining a phantom having one or more known optical characteristics; (ii) inserting the phantom into a first imaging system; (iii) imaging the phantom in the first system to obtain first image data of $S(\lambda_x)$ and $S(\lambda_{x+}\lambda_m)$; (iv) inserting the phantom into a second imaging system; (v) imaging the phantom in the second imaging system to obtain second image data system to obtain second image data of $S(\lambda_x)$ and ($S(\lambda_x+\lambda_m)$; (vi) and comparing the first and second image data to compare the two systems.

In some embodiments, a method of training an operator of a fluorescence imaging camera and detection system, the said method comprising obtaining a scattering phantom having one or more known optical characteristics; inserting the phantom into an imaging system; operating the system to image and analyze the phantom, thereby assisting in the training the operator. In some embodiments a solid phantom and measurement approach for the quantification of excitation light leakage and measurement sensitivity of fluorescence imaging devices. In some embodiments the solid phantom, comprises coating of stable fluorescent material, including, but not limited to, fluorescent metals, fluorescent semiconductor material, organic and inorganic fluorescent quantum dots, as well as organic and inorganic materials such as, but not limited to, Alexa Fluor, IR-Iodide, or lanthanide onto a specularly reflective surface that are stable and can be used as a traceable fluorescence standard. With a constructed solid phantom, the intensified CCD (ICCD)-based device demonstrated more than 300% higher measurement sensitivity compared to the Electron Multiplying CCD (EMCCD) based device when integration time was maintained less than 1.0 s.

In some embodiments, a method is provided comprising preparing a solid phantom, placing the solid phantom under a fluorescence imaging camera system, measuring reflected and scattered excitation light and fluorescent light from different portions of the phantom, determining the proportion of fluorescent versus reflected and scattered excitation light collected and computing a ratio of fluorescent versus reflected (scattered excitation) light or SNR to ascertain level of sensitivity of the system. Such measurements provide objective standards that can be used to, among other things, determine whether the performance of the camera system is satisfactory for use on living tissues or tissue specimens, to determine the performance of fluorescence imaging systems, to perform installation and operational qualification, to compare between systems, and day to day validation that the system is operating up to standard (quality control). In some embodiment the inorganic quantum dot 800 is replaced with different quantum dots or semiconductor materials depending on the operating wavelengths of the fluorescence imaging camera system.

In some embodiments, is a 2 dimensional solid phantom for use with fluorescence imaging camera systems. In some embodiments, a solid phantom comprises stable fluorescent material, painted, layered, or incorporated on a calibrated diffuse reflectance target. In some embodiments, a solid phantom further comprises polyurethane. In some embodiments, a method of making a solid phantom comprising: preparing a solution of stable fluorescent material, semiconductor materials or quantum dots; diluting with a polyurethane solution to dilute to 0.1 uM; and coating the reflectance target such that the reflectance value of said target simulates 99% of the worst case scenario observed with a test article. In some embodiments, the phantom comprises a stable fluorescent material that is sprayed on the calibrated diffuse reflectance target. In some embodiments the phantom comprises a calibrated diffuse reflectance target that is dipped in a solution comprising stable fluorescent material. In some embodiments, the reflectance value of said target simulates 99%, 98%, 97%, 96%, 95%, 90%, 85%, 80%, 75%, 70% 65%, 60%, 55%, 50%, 25%, 10% or 0%. In some embodiments, is a method of quantitatively characterizing the transmission ratio (TR) and the signal-to-noise ratio of a fluorescence imaging camera system, the method comprising: placing the phantom under a fluorescence imaging camera system; determining the transmission ratio to quantify excitation light leakage; and determining the signal-to-noise ratio. In other embodiments, a method of evaluating the sensitivity of a fluorescence imaging camera system, comprising: placing the phantom under a fluorescence imaging camera system; measuring reflected light from different portions of the phantom; measuring fluorescent from different portions of the phantom; and computing a ratio of fluorescent light versus backscattered excitation light to ascertain the level of sensitivity of the system. In some embodiments, a method of validating that a fluorescence imaging camera system is operating at an acceptable level. In some embodiments, a method of comparing two or more fluorescence imaging camera systems, said method comprising: obtaining the phantom of having one or more known optical characteristics; inserting the phantom into a first imaging system; imaging the phantom in the first system to obtain first image data; inserting the phantom into a second imaging system; imaging the phantom in the second system to obtain second image data; and comparing the first and second image data to compare the two systems. In some embodiments, a method of training an operator of a fluorescence imaging camera system, said method comprising obtaining a tissue-like phantom having one or more known optical characteristics; inserting the phantom into an imaging system; operating the system to image and analyze the phantom, thereby training the user. In some embodiments, a solid phantom where the stable fluorescent material is painted on said calibrated diffuse reflectance target. In some embodiments, a phantom wherein stable fluorescent material is sprayed on said calibrated diffuse reflectance target. In some embodiments, a phantom where the calibrated diffuse reflectance target is dipped in a solution comprising stable fluorescent material. In some embodiments, a 2 dimensional solid phantom for use with fluorescence imaging camera systems that are designed to detect fluorescence in scattering media such as living tissues.

The following section provides further details regarding examples of various embodiments. It should be appreciated by those of skill in the art that the techniques disclosed in the examples that follow represent techniques and/or compositions discovered by the inventor to function well in the practice of the invention. However, those of skill in the art should, in light of the present disclosure, appreciate that many changes can be made in the specific embodiments which are disclosed and still obtain a like or similar result without departing from the spirit and scope of the invention. These examples are illustrations of the methods and systems described herein and are not intended to limit the scope of the invention.

EXAMPLES

Example 1

Description of Imaging Systems

Figure 3:
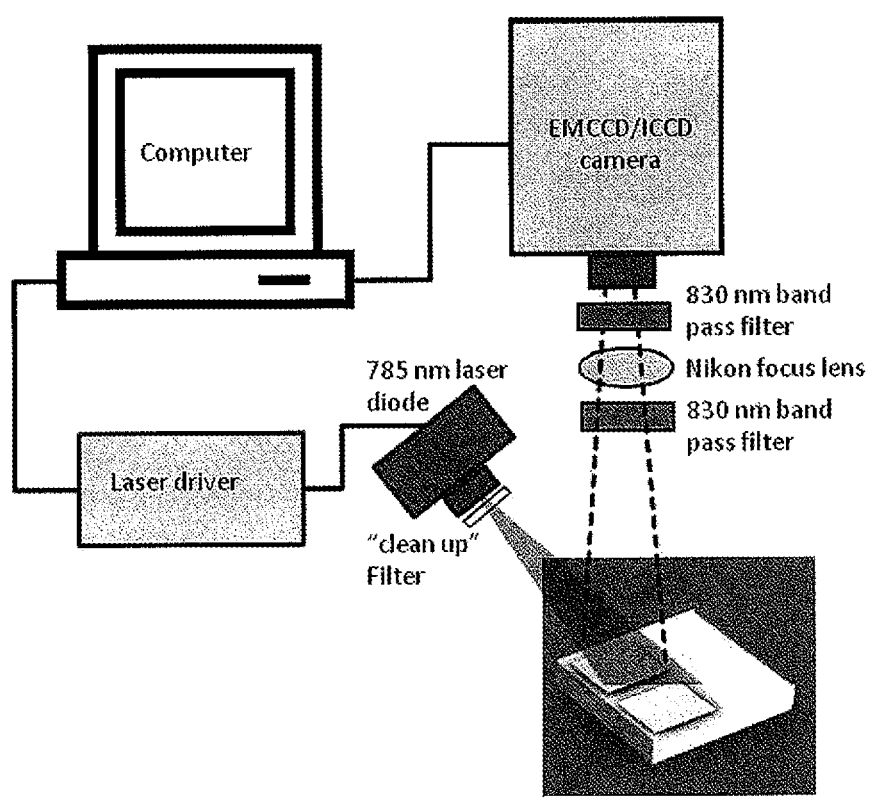
FIG. 3: Illustrates a schematic of Electron Multiplying Charge Coupled Device (EMCCD) and Intensified Charge Coupled Device (ICCD) based NIR fluorescence imaging systems.

Illustrated in FIG. 3 is an Electron Multiplying Charge Coupled Device (EMCCD) and Intensified Charge Coupled Device (ICCD) based NIR fluorescence imaging system. Excitation illumination was provided by a 785 nm laser diode (HPD1005-9 mm-78503 model, High Power Devices Inc., NJ) outfitted with a 785 nm band pass "clean-up" filter (LD01-785/10, optical density>5 at 705-765 nm and 803-885 nm, Semrock, Inc.), an optical diffuser and a convex lens to provide uniform illumination over 176 cm$^2$ area. The collected fluorescent signals were filtered using two 830 nm band pass filters (830FS10, optical density >5 at 785 nm, Andover, Salem, N.H.) separated with the Nikon focus lens (AF NIKKOR 28 mm f/2.8D, Nikon, N.Y., USA) to increase the optical density at the excitation wavelength in order to reduce the leakage of excitation light. The filtered fluorescence signals were amplified and recorded by the Electron Multiplying Charge Coupled Device (EMCCD: PhotonMax, Photometrics, Tucson, Ariz.) and custom Intensified Charge Coupled Device (ICCD: 9), respectively. The Electron Multiplying Charge Coupled Device (EMCCD) camera and Intensified Charge Coupled Device (ICCD) camera were cooled to −70° C. and −25° C., respectively. The imaging processes were implemented under LabVIEW based interface (National Instruments, Austin, Tex.).

Example 2

Construction of Qdot® 800 ITK™ Fluorescence Solid Phantom

A solid phantom was made of quantum dots (Qdot® 800 ITK™, Q21771MP, Invitrogen, Carlsbad, Calif.) were painted on a calibrated diffuse reflectance target (SRT-99-020, Labsphere, Inc., North Sutton, N.H.). The reflectance value of the target was 99%, simulating the worse-case scenario for multiply scattered light that contributes to excitation light leakage. Qdot® 800 ITK™ was chosen due to their stability and their NIR emission spectra following excitation across a broad spectral range from visible to NIR. Polyurethane was chosen as a base to adhere the Qdot® 800 ITK™ dye to the surface of the reflectance target. Alternative base resins include, but are not limited to other polyurethanes, polyester resins and epoxy-resins, the use of which is determined by the properties of the stable fluorescent material selected for a particular imaging system.

Figure 4:
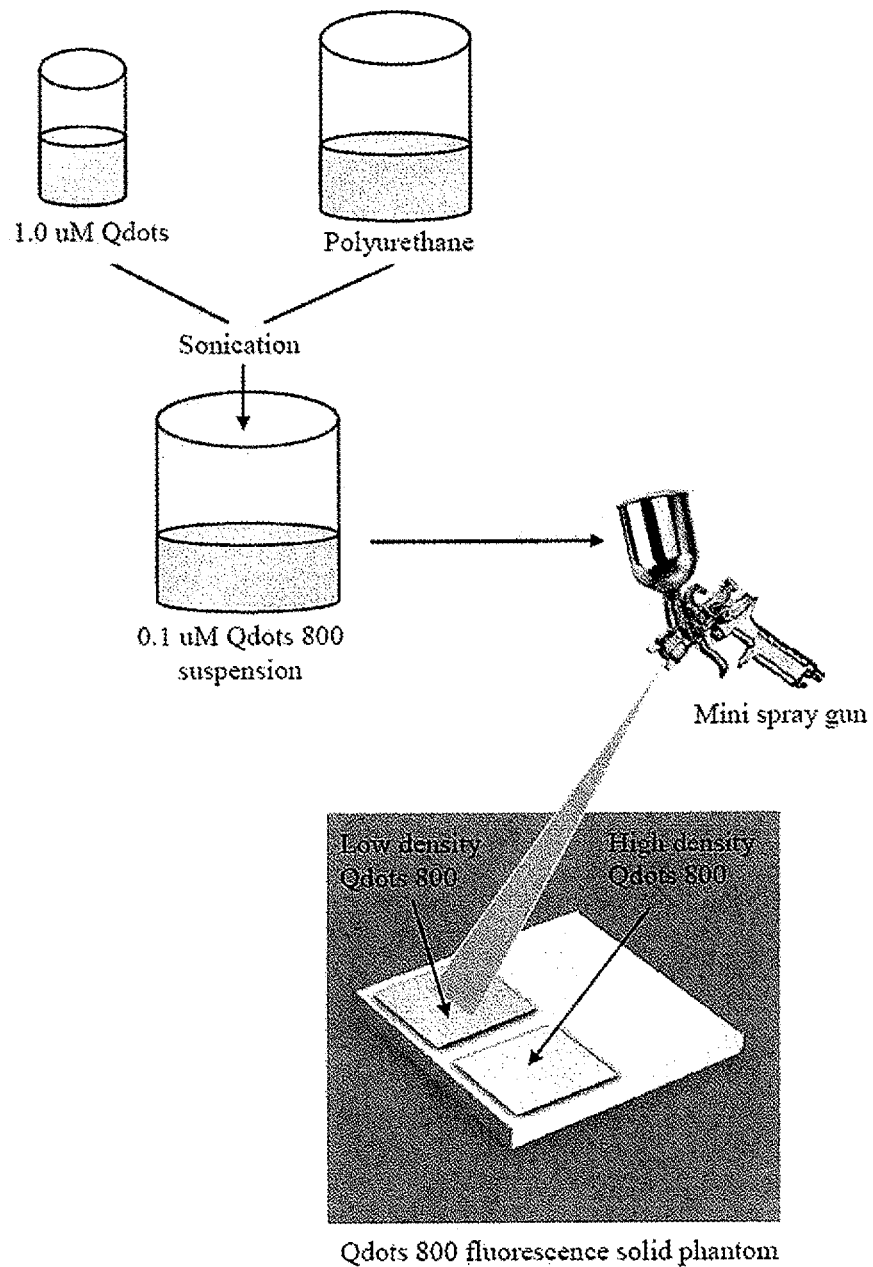
FIG. 4: Illustrates the Qdot® 800 ITK™ fluorescence solid phantom construction process.

The phantoms were constructed is as follows: A 1.0 uM solution of Qdot® 800 ITK™: in decane was diluted to 0.1 uM by adding polyurethane solution (Interior Oil-Based Polyurethane #18012 Satin, Cabot, Newburyport, Mass., USA). The solution was mixed by hand (or using a sonicator (Vortex Genie-2, Scientific Industries, NY, USA)). The mixture then was poured into a spray gun (Model H7670, Grizzly Industrial Inc., WA) and was sprayed onto the surface of the reflectance target. Another reflective target without Qdot® 800 ITK™ added was used to create the phantom for measuring $S(\lambda_x)$. FIG. 4 is a schematic of the process used to construct Qdot® 800 ITK™ fluorescence solid phantom. To provide a measurement of dynamic range, varying densities of Qdot® 800 ITK™ can be applied. Throughout the present disclosure three types of phantoms were used: (i) phantoms comprising a reflective target that were subjected to a high density (10×-20×) application of Qdot® 800 ITK™; (ii) phantoms comprising a reflective target that were subjected to a low density (1×) application of Qdot® 800 ITK™; and (iii) phantoms comprising a reflective target without Qdot® 800 ITK™ application. The density of the application of quantum dots (or stable fluorescent material) depends upon the concentration of material sprayed, the duration of the spray application, the number of coats, etc., and is quantified through any number of analytical methods including transmission electron microscopy as well as other techniques.

Example 3

Stability of Qdot® 800 ITK™ Fluorescence Solid Phantom Over Time

Figure 5:
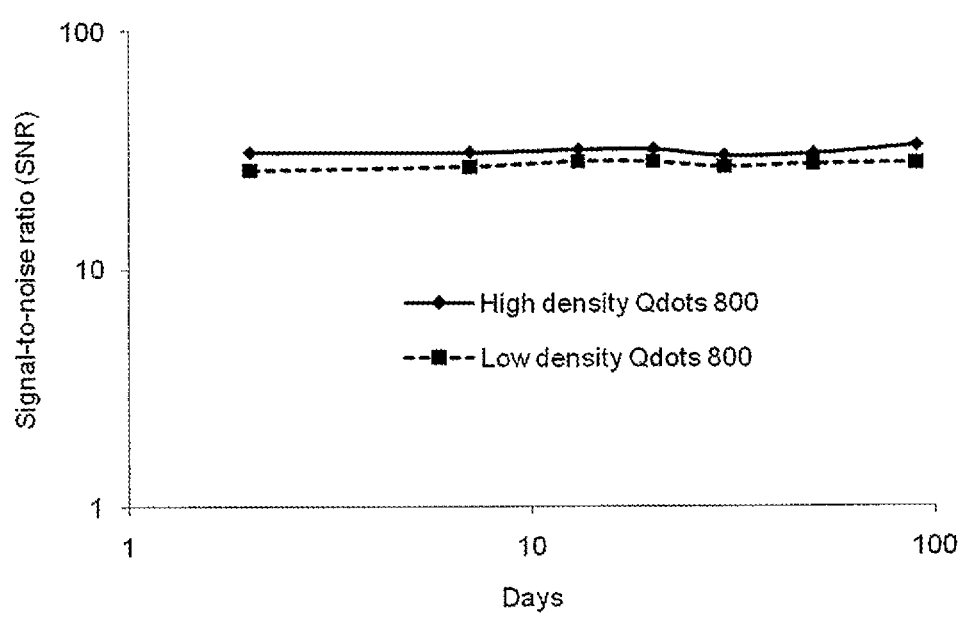
FIG. 5: Illustrates the signal-to-noise ratio (SNR) of a Intensified Charge Coupled Device (ICCD)-based device on the constructed fluorescence phantom as a function of time.

To assess phantom stability, signal-to-noise ratio (SNR) was measured as a function of time using the Intensified Charge Coupled Device (ICCD) imaging system described above. When not used, the phantom was stored in a light-tight container with a desiccant, and maintained at room temperature. FIG. 5 depicts the calculated signal-to-noise ratio (SNR) on the high and low density Qdot® 800 ITK™ regions using the Intensified Charge Coupled Device (ICCD) based NIR fluorescence imaging system as a function of time. The results show that no degradation in the signal-to-noise ratio was observed over a period of three months, indicating that phantom remains stable to within <10% variations and this may be due to instrumentation variability over time. Therefore, the phantom is a stable alternative as compared to the stability of liquid lipid and dye phantoms commonly used to assess device performance which are measure in hours.

Example 4

Transmission Ratio (R) and Signal-to-Noise Ratio (SNR)

To evaluate the excitation light leakage and measurement sensitivity of Electron Multiplying Charge Coupled Device (EMCCD) and Intensified Charge Coupled Device (ICCD)-based NIR fluorescence imaging devices, R and signal-to-noise ratio values were measured using the constructed Qdot® 800 ITK™ fluorescence/reflectance solid phantom. Values of R and signal-to-noise ratio were obtained as a function of the gain, CCD camera integration time, and laser power. In all cases, the laser power was adjusted to less than 1.9 mW/cm$^2$ or the maximum permissible incidence level established by our approved Food and Drug Administration (FDA) investigational new drug applications which cover for our clinical studies. Because motion artifacts prevent long CCD camera integration time in clinical settings, integration times were 1.0 s.

Example 5

Figure 6:
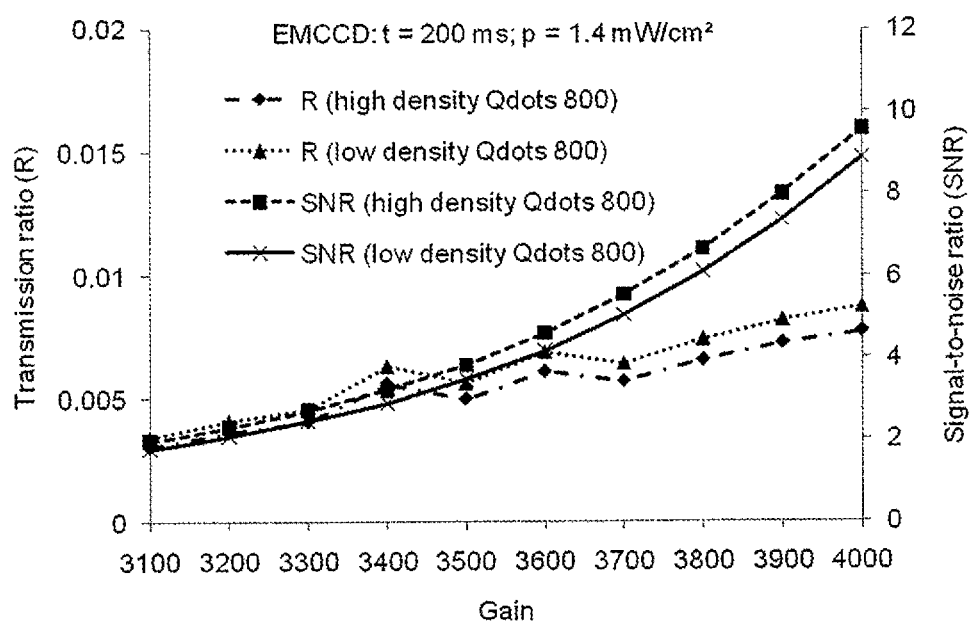
FIG. 6: Illustrates that the obtained transmission ratio (R) and signal-to-noise ratio (SNR) obtained for a Electron Multiplying Charge Coupled Device (EMCCD) based NIR fluorescence imaging system as a function of gain, where t and p represent the CCD camera integration time and laser power.
Figure 7:
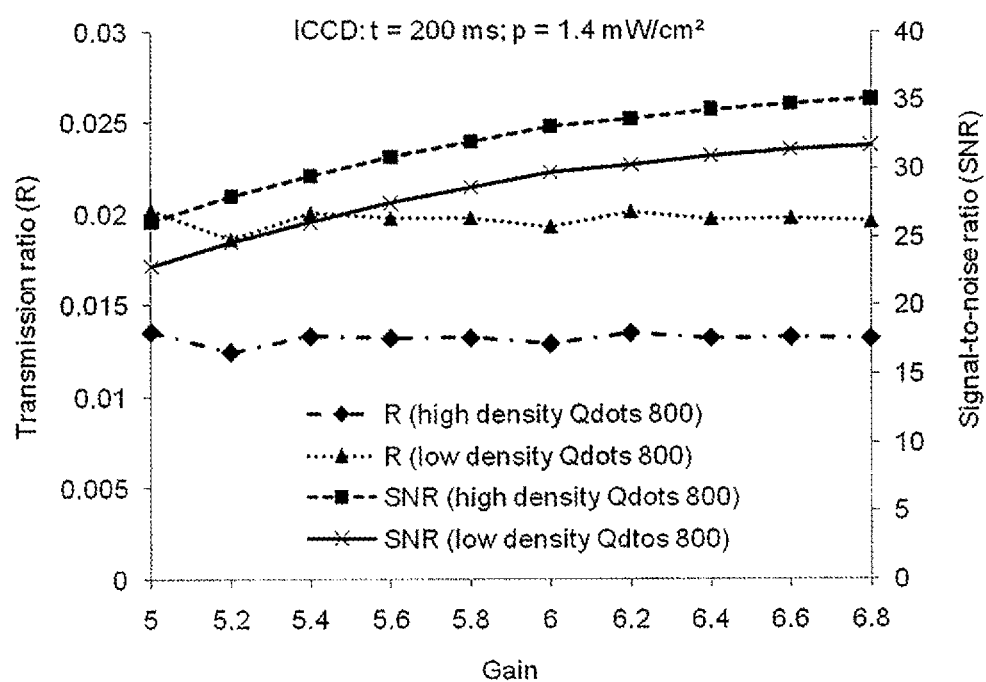
FIG. 7: Illustrates that the obtained transmission ratio (R) and signal-to-noise ratio (SNR) obtained for a the Intensified Charge Coupled Device (ICCD) based NIR fluorescence imaging system as a function of gain, where t and p represent the CCD camera integration time and laser power, and the gain value in the Intensified Charge Coupled Device (ICCD) camera is the voltage supplied to the high power supply for the intensifier with range from 1 to 10.
Figure 8:
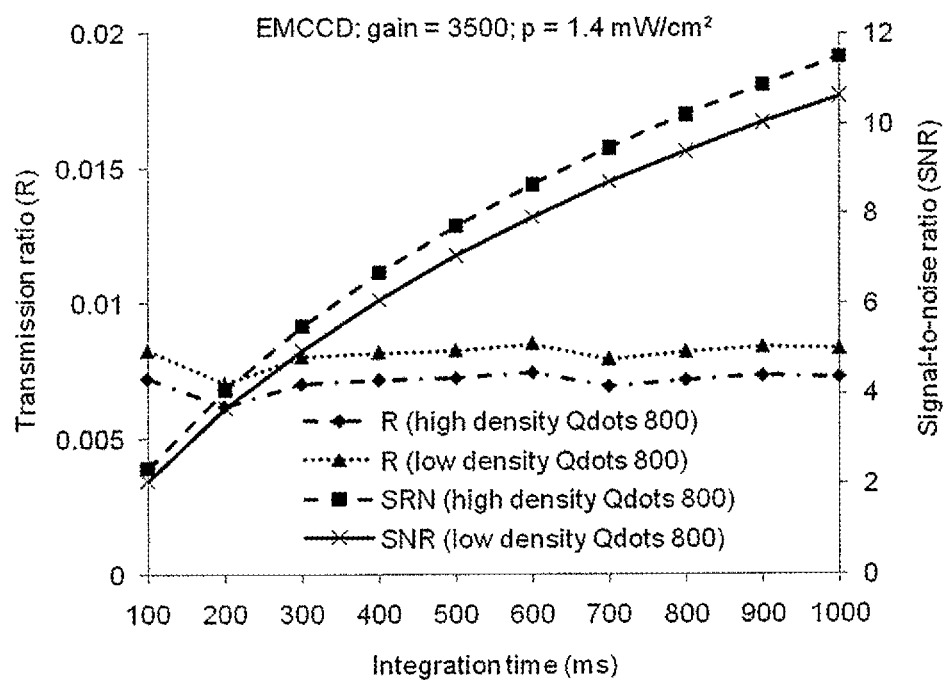
FIG. 8: Illustrates that the obtained transmission ratio (R) and signal-to-noise ratio (SNR) obtained for a Electron Multiplying Charge Coupled Device (EMCCD) based NIR fluorescence imaging system as a function of CCD camera integration time, where t and p represent the CCD camera integration time and laser power.
Figure 9:
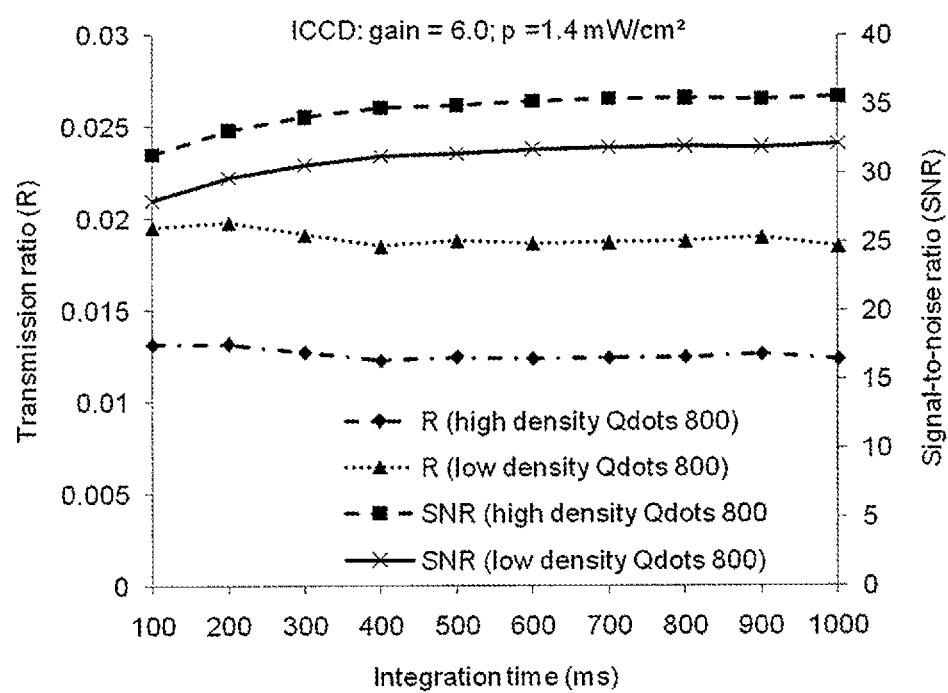
FIG. 9: Illustrates that the transmission ratio (R) and signal-to-noise ratio (SNR) obtained for a Intensified Charge Coupled Device (ICCD) based NIR fluorescence imaging system as a function of CCD camera integration time, where t and p represent the CCD camera integration time and laser power, and the gain value in the Intensified Charge Coupled Device (ICCD) camera is the voltage supplied to the high power supply for the intensifier with range from 1 to 10.
Figure 10:
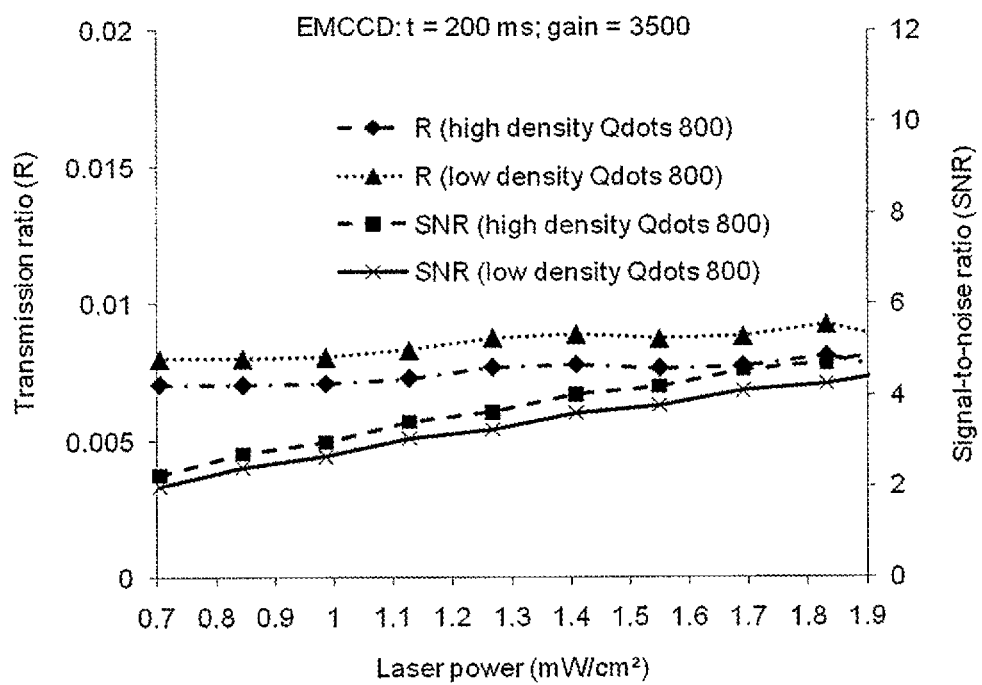
FIG. 10: Illustrates that the transmission ratio (R) and signal-to-noise ratio (SNR) obtained for a Electron Multiplying Charge Coupled Device (EMCCD) based NIR fluorescence imaging system as a function of laser power, where t and p represent the CCD camera integration time and laser power.
Figure 11:
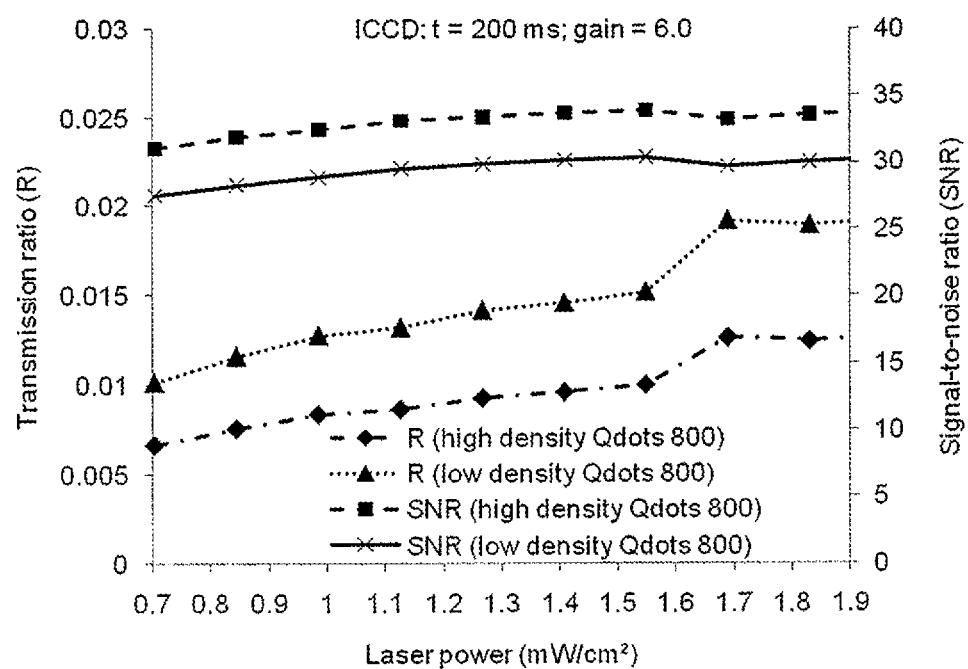
FIG. 11: Illustrates that the transmission ratio (R) and signal-to-noise ratio (SNR) obtained for a Intensified Charge Coupled Device (ICCD) based NIR fluorescence imaging system as a function of laser power, where t and p represent the CCD camera integration time and laser power, and the gain value in the Intensified Charge Coupled Device (ICCD) camera is the voltage supplied to the high power supply for the intensifier with range from 1 to 10.

Values of Transmission Ratio (R) and Signal-to-Noise Ratio (SNR) in Electron Multiplying Charge Coupled Device (EMCCD) and Intensified Charge Coupled Device (ICCD)-Based Devices FIGS. 6-11 depict values of transmission ratio, R, and signal-to-noise ratio of the Electron Multiplying Charge Coupled Device (EMCCD) and Intensified Charge Coupled Device (ICCD) based NIR fluorescence imaging systems as a function of gain (FIGS. 6 and 7, respectively), CCD camera integration time (FIGS. 8 and 9, respectively), and laser power (FIGS. 10 and 11, respectively). The magnitude of R depends on the gain of Electron Multiplying Charge Coupled Device (EMCCD) as shown in FIG. 6 and may be due to the nonlinear response of Electron Multiplying Charge Coupled Device (EMCCD) camera on the input signals. As the Electron Multiplying Charge Coupled Device (EMCCD) gain increases, the proportion of "leaked" excitation light may be more heavily weighted. In contrast, as shown in FIG. 8 the magnitude of transmission ratio, R, is independent of the integration time of the Electron Multiplying Charge Coupled Device (EMCCD) based imaging device and, as shown in FIGS. 7 and 9, independent of intensifier gain and integration time of the Intensified Charge Coupled Device based imaging device.

The lack of dependence on R is expected since the detected "true" fluorescence (or values of $(S(\lambda_x+\lambda_m)-S(\lambda_x))$ and "leaked" excitation light (or values of $S(\lambda_x+\lambda_m)$) are both approximately proportional to the intensifier gain and CCD camera integration time for the small range of wavelengths (i.e., $\lambda_x$ and $\lambda_m$). As expected, a higher laser power results in increased excitation light leakage in both Electron Multiplying Charge Coupled Device (EMCCD) and Intensified Charge Coupled Device (ICCD) based NIR fluorescence imaging systems, as shown in FIGS. 10 and 11.

From Equation (1), it can be seen that as the density of Qdot® 800 ITK™ (or stable fluorescent material) is reduced, one would expect an increase in the values of transmission ratio, R, since the 'leaked" excitation light can be considered as constant when all other experimental parameters are constant. This trend was seen in the increased values of transmission ratio (R) for low as compared to high densities of Qdot® 800 ITK™ in FIGS. 6 and 7. The values of transmission ratio (R) measured for all experimental cases are less than 0.02, indicating that the measured fluorescence signals dominate over the excitation light leakage. The value of transmission ratio (R) may provide a standard metric for quantification of excitation light leakage in NIR fluorescence based imaging devices. Although the same filter set was employed for separating fluorescence signals from strong backscattered excitation light, the values of transmission ratio, R, measured using the Electron Multiplying Charge Coupled Device (EMCCD) based device were always less than that of Intensified Charge Coupled Device (ICCD) based device for each experimental cases.

As shown in FIGS. 7, 9 and 11, the signal-to-noise ratio performance in Intensified Charge Coupled Device-based device continuously improved with increasing the gain, integration time and laser power and easily reached its shot-noise limit, beyond which the signal-to-noise ratio is constant, indicating that the shot noise overwhelms the other noise sources. Although the signal-to-noise ratio performance in Electron Multiplying Charge Coupled Device (EMCCD)-based device increases with gain, integration time, and laser power as shown in FIGS. 6, 8, and 10, the system is not shot-noise limited and the readout noise is the dominant limiting factor. In all cases, the Intensified Charge Coupled Device (ICCD)-based device provides higher signal-to-noise ratio and better measurement sensitivity compared to that of Electron Multiplying Charge Coupled Device (EMCCD)-based device, which is consistent with the transmission ratio, R. The higher measurement sensitivity may be due to the higher gain provided by the intensifier of Intensified Charge Coupled Device (ICCD) camera than of multiplication register of Electron Multiplying Charge Coupled Device (EMCCD) camera.

Figure 12:
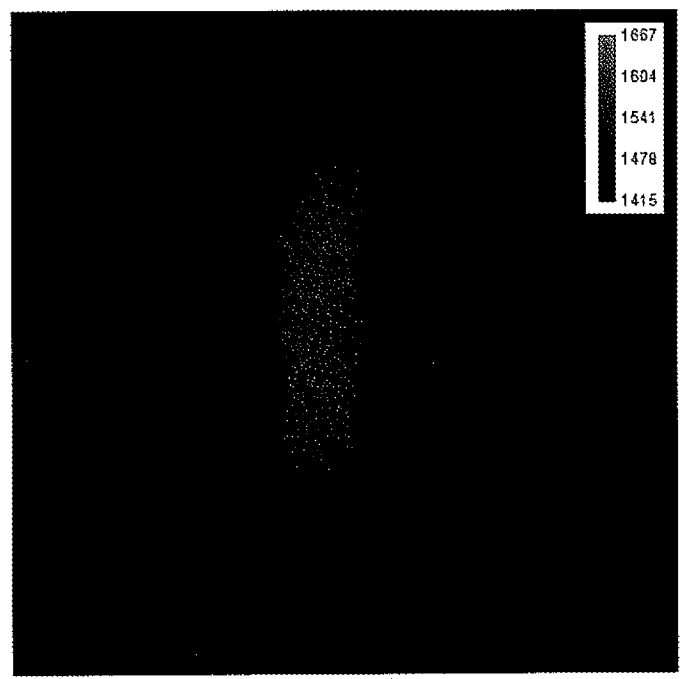
FIG. 12: Illustrates fluorescence images acquired with Electron Multiplying Charge Coupled Device (EMCCD) based NIR fluorescence devices showing an Eppendorf tube filled with 1.0 nM ICG in 1.0% Liposyn solution.
Figure 13:
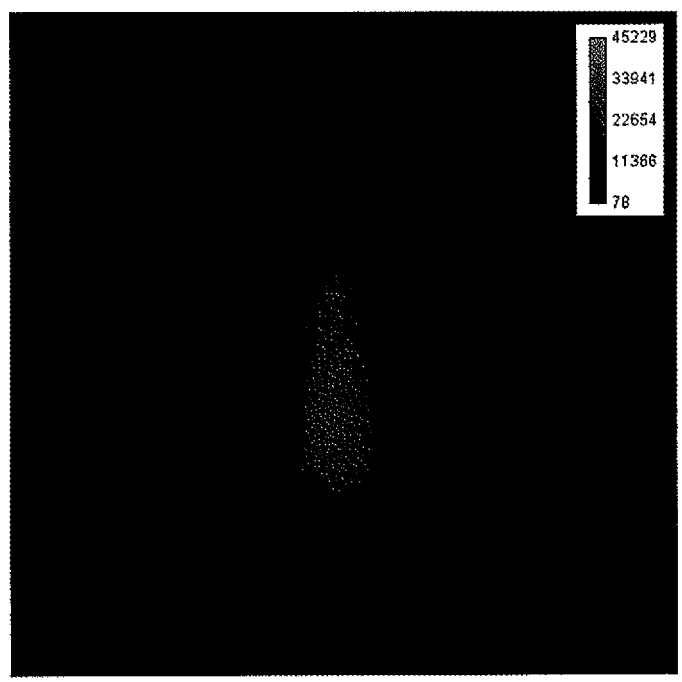
FIG. 13: Illustrates fluorescence images acquired with Intensified Charge Coupled Device (ICCD) based NIR fluorescence devices showing an Eppendorf tube filled with 1.0 nM ICG in 1.0% Liposyn solution.

Comparative performance in Electron Multiplying Charge Coupled Device (EMCCD) and Intensified Charge Coupled Device (ICCD) developed with the solid phantom mimic with the intralipid phantoms used by others FIGS. 12 and 13 illustrate the comparative performance of the Electron Multiplying Charge Coupled Device (EMCCD) and Intensified Charge Coupled Device (ICCD) based devices in which a 1.0 nM ICG in 1.0% Liposyn solution mimicking scattering properties of tissue is compared with identical laser power and integration times. Even with the gain of the Electron Multiplying Charge Coupled Device (EMCCD) camera set to maximum value to obtain as high signal-to-noise ratio as possible, the measured fluorescence signal is low and contaminated by a higher noise floor when compared to that from Intensified Charge Coupled Device (ICCD) and may account for the reported higher sensitivity using NIR sensitive Intensified Charge Coupled Device (ICCD) devices as opposed to Electron Multiplying Charge Coupled Device (EMCCD) devices.

Without further elaboration, it is believed that one skilled in the art can, using the description herein, utilize the present invention to its fullest extent. The embodiments described herein are to be construed as illustrative and not as constraining the remainder of the disclosure in any way whatsoever. While the preferred embodiments have been shown and described, many variations and modifications thereof can be made by one skilled in the art without departing from the spirit and teachings of the invention. For example, although the described embodiments illustrate use of the present compositions and methods on humans, those of skill in the art would readily recognize that these methods and compositions could also be applied to veterinary medicine and other mammals. Accordingly, the scope of protection is not limited by the description set out above, but is only limited by the claims, including all equivalents of the subject matter of the claims. The disclosures of all patents, patent applications and publications cited herein are hereby incorporated herein by reference, to the extent that they provide procedural or other details consistent with and supplementary to those set forth herein.

REFERENCES CITED

The following references, to the extent that they provide exemplary procedural or other details supplementary to those set forth herein, are specifically incorporated herein in their entirety by reference: U.S. Pat. No. 5,865,754; U.S. Pat. No. 7,054,002; U.S. Pat. No. 7,328,059; US Pat Appl. No. 2007/0286468; US Pat. Appl. No. 2008/0056999; US Pat. Appl. No. 2008/0064954; US Pat. Appl. No. 2008/0175790; US Pat. Appl. No. 2011/007140; and non-patent documents: Sharma, R., Wang, W., Rasmussen, J. C., Joshi, A., Houston, J. P., Adams, K. E., Cameron, A., Ke, S., Kwon, S., Mawad, M. E & Sevick Muraca, E. M. Quantitative imaging of lymph function. *Am J Physiol Heart Circ Physiol* 292, H3109 (2007); Kwon, S. & Sevick-Muraca, E. M. Noninvasive quantitative imaging of lymph function in mice. *Lymphat Res Biol* 5, 219-232 (2007); Rasmussen, J. C., Tan, I., Marshall, M. V., Fife, C. E. & Sevick Muraca, E. M. Lymphatic imaging in humans with near-infrared fluorescence. *Curr Opin Biotechnol* 20, 74-82 (2009); Rasmussen, J. C., Tan, I. C., Marshall, M. V., Adams, K. E., Kwon, S., Fife, C. E., Maus, E. A., Smith, L. A., Covington, K. R. & Sevick-Muraca, E. M. Human lymphatic architecture and dynamic transport imaged using near-infrared fluorescence. *Transl Oncol* 3, 362-372 (2010); Tan, I., Maus, E. A., Rasmussen, J. C., Marshall, M. V., Adams, K. E., Fife, C. E., Smith, L. A., Chan, W. & Sevick Muraca, E. M. Assessment of lymphatic contractile function after manual lymphatic drainage using near-infrared fluorescence imaging. *Arch Phys Med Rehabil* 92, 756-764 (2010); Adams, K. E., Rasmussen, J. C., Darne, C., Tan, I., Aldrich, M. B., Marshall, M. V., Fife, C. E., Marshall, M. V., Smith, L. A., R., G., S., H. & Sevick Muraca, E. M. Direct evidence of lymphatic function improvement after advanced pneumatic compression device treatment of lymphedema. *Biomed Opt Express* 1, 114-125 (2010); Maus, E. A., Tan, I., Rasmussen, J. C., Marshall, M. V., Fife, C. E., Smith, L. A., Gurfinkel, M. & Sevick Muraca, E. M. Near infrared fluorescence imaging of lymphatics in head and neck lymphedema. *Head & Neck* (2010); Marshall, M. V., Rasmussen, J. C., Tan, I. C., Aldrich, M. B., Adams, K. E., Wang, X., Fife, C. E., Maus, E. A., Smith, L. A. & Sevick-Muraca, E. M. Near-infrared fluorescence imaging in humans with indocyanine green: a review and update. *Open Surg Oncol J* 2, 12-25 (2010); Sevick-Muraca, E. M., Sharma, R., Rasmussen, J. C., Marshall, M. V., Wendt, J. A., Pham, H. Q., Bonefas, E., Houston, J. P., Sampath, L. & Adams, K. E. Imaging of Lymph Flow in Breast Cancer Patients after Microdose Administration of a Near-Infrared Fluorophore: Feasibility Study. *Radiology* 246, 734-741 (2008); Sevick-Muraca, E. M. & Rasmussen, J. C. Molecular imaging with optics: primer and case for near-infrared fluorescence techniques in personalized medicine. *J Biomed Opt* 13, 041303 (2008); Sahu, A. K., Roy, R., Joshi, A. & Sevick-Muraca, E. M. Evaluation of anatomical structure and non-uniform distribution of imaging agent in near-infrared fluorescence-enhanced optical tomography. *Opt Express* 13, 10182-10199 (2005); Sevick Muraca, E. M., Lopez, G., Reynolds, J. S., Troy, T. L. & Hutchinson, C. L. Fluorescence and Absorption Contrast Mechanisms for Biomedical Optical Imaging Using Frequency Domain Techniques. *Photochem Photobiol* 66, 55-64 (1997); Li, X., Chance, B. & Yodh, A. G. Fluorescent heterogeneities in turbid media: limits for detection, characterization, and comparison with absorption. *Appl. Opt.* 37, 6833-6844 (1998); Hutteman, M., Choi, H. S., Mieog, J. S. D., van der Vorst, J. R., Ashitate, Y., Kuppen, P. J. K., van Groningen, M. C., Lowik, C. W. G. M., Smit, V. T., van de Velde, C. J. H., V., F. J. & L., L. A. Clinical translation of ex vivo sentinel lymph node mapping for colorectal cancer using invisible near-infrared fluorescence light. *Ann Surg Oncol* 18, 1006-1014 (2011); Hwang, K., Houston, J. P., Rasmussen, J. C., Joshi, A., Ke, S., Li, C. & Sevick-Muraca, E. M. Improved excitation light rejection enhances small-animal fluorescent optical imaging. *Mol Imaging* 4, 194-204 (2005); Zhu, B., Rasmussen, J. C., Lu, Y. & Sevick-Muraca, E. M. Reduction of excitation light leakage to improve near-infrared fluorescence imaging for tissue surface and deep tissue imaging. *Med Phys* 37, 5961-5970 (2010); Zhu, B. & Sevick-Muraca, E. M.

Minimizing excitation light leakage and maximizing measurement sensitivity for molecular imaging with near-infrared fluorescence. *J Innov Opt Health Sci* 4, 301-307 (2011); Houston, J. P., Thompson, A. B., Gurfinkel, M. & Sevick Muraca, E. M. Sensitivity and Depth Penetration of Continuous Wave Versus Frequency domain Photon Migration Near infrared Fluorescence Contrast-enhanced Imaging. *Photochem Photobiol* 77, 420-430 (2003); Dussault, D. & Hoess, P. Noise Performance Comparison of ICCD and EMCCD Cameras. *Proc. SPIE* 5563, 195-204 (2004); Ntziachristos, V. & Weissleder, R. Experimental three-dimensional fluorescence reconstruction of diffuse media by use of a normalized Born approximation. Opt Lett 26, 893-895 (2001); and Ge, J., Zhu, B., Regalado, S., & Godavarty, A. Three-dimensional fluorescence-enhanced optical tomography using a hand-held probe based imaging system. Med Phys 35, 3354-63 (2008).

What is claimed is:

1. A 2-dimensional solid phantom for use with fluorescence imaging camera systems, where said phantom comprises: a stable fluorescent material wherein the stable fluorescence material comprises: a semiconductor material; quantum dots; or a combination thereof; and a calibrated diffuse reflectance target; and wherein said use comprises evaluating sensitivity of fluorescence detection of said camera systems; or quantitatively characterizing the transmission ratio and the signal-to-noise ratio of a said fluorescence imaging camera system.

2. The phantom of claim 1, wherein said phantom further comprises polyurethane.

3. A method of making the solid phantom of claim 2, said method comprising:
    diluting a stable fluorescence material with a polyurethane solution and forming a solution of the stable fluorescence material with a first concentration; and
    coating said reflectance target with said solution such that the reflectance value of said target is about 99%.

4. The method of making a phantom of claim 3, wherein said stable fluorescent material is sprayed on said reflectance target.

5. The method of making a phantom of claim 3, wherein said reflectance target is dipped in a solution comprising the stable fluorescent material.

6. The method of making a solid phantom of claim 3, wherein said stable fluorescent material is painted on said reflectance target.

7. The method of making a phantom of claim 3, wherein stable fluorescent material is sprayed on said reflectance target.

8. The method of making a phantom of claim 3, wherein said reflectance target is dipped in a solution comprising stable fluorescent material.

9. The method of claim 3, wherein the first concentration is about 0.01 μm to about 1 μm.

10. The method of claim 3, wherein the first concentration is about 0.1 uM.

11. The phantom of claim 1, wherein the target comprises a reflectance value of about 99%, 98%, 97%, 96%, 95%, 90%, 85%, 80%, 75%, 70% 65%, 60%, 55%, 50%, 25%, 10% or 0%.

12. A method of training an operator of a fluorescence imaging camera system, said method comprising obtaining a phantom of claim 1, having one or more known optical characteristics; inserting the phantom into an imaging system; operating the system to image and analyze the phantom, thereby training the user.

13. The method of claim 12, wherein the phantom comprises a reflectance value of a tissue.

14. The 2 dimensional solid phantom of claim 1, wherein said fluorescence imaging camera systems are designed to detect fluorescence in scattering media, wherein said scattering media is a living tissues.

15. A method of quantitatively characterizing the transmission ratio and the signal-to-noise ratio of a fluorescence imaging camera system, said method comprising:
    (i) placing a 2 dimensional solid phantom for use with fluorescence imagine camera systems under said fluorescence imaging camera system;
    (ii) determining the transmission ratio, and quantifying an excitation light leakage; and
    (iii) determining the signal-to-noise ratio.

16. A method of evaluating the sensitivity of a fluorescence imaging camera system, said method comprising:
    (i) placing a 2 dimensional solid phantom for use with fluorescence imagine camera systems under said fluorescence imaging camera system;
    (ii) measuring reflected light from different portions of the phantom;
    (iii) measuring fluorescent from different portions of the phantom; and
    (iv) computing a ratio of fluorescent light versus backscattered excitation light, and quantifying the level of sensitivity of the system.

17. A method of validating that a fluorescence imaging camera system is operating at an acceptable level using a method of evaluating the sensitivity of a fluorescence imaging camera system, said method comprising:
    (i) placing a 2 dimensional solid phantom for use with fluorescence imagine camera systems under said fluorescence imaging camera system;
    (ii) measuring reflected light from different portions of the phantom;
    (iii) measuring fluorescent from different portions of the phantom; and
    (iv) computing a ratio of fluorescent light versus backscattered excitation light, and quantifying the level of sensitivity of the system, wherein the ratio of fluorescent light versus backscattered excitation light, is compared to a predefined standard.

18. A method of comparing two or more fluorescence imaging camera systems, said method comprising:
    (i) obtaining a 2 dimensional solid phantom for use with fluorescence imagine camera systems having one or more known optical characteristics;
    (ii) inserting the phantom into a first imaging system;
    (iii) imaging the phantom in the first system to obtain first image data;
    (iv) inserting the phantom into a second imaging system;
    (v) imaging the phantom in the second system to obtain second image data; and
    (vi) comparing the first and second image data to compare the two systems.

* * * * *